United States Patent [19]
Kilmer et al.

[11] Patent Number: 5,368,604
[45] Date of Patent: * Nov. 29, 1994

[54] METHOD AND APPARATUS FOR SURGICALLY PROFILING THE CORNEA USING VACUUM

[75] Inventors: Lauren G. Kilmer; Alvin E. Reynolds, both of Tulsa, Okla.

[73] Assignee: Corneal Contouring Inc., Azusa, Calif.

[*] Notice: The portion of the term of this patent subsequent to Nov. 12, 2008 has been disclaimed.

[21] Appl. No.: 170,679

[22] Filed: Dec. 20, 1993

Related U.S. Application Data

[63] Continuation of Ser. No. 939,856, Sep. 2, 1992, abandoned, which is a continuation of Ser. No. 894,162, Jun. 3, 1992, abandoned, which is a continuation of Ser. No. 592,601, Oct. 4, 1990, abandoned, which is a continuation-in-part of Ser. No. 450,672, Dec. 14, 1989, Pat. No. 5,063,942.

[51] Int. Cl.$^5$ ................................. A61F 9/00
[52] U.S. Cl. ................................. 606/166; 606/161; 606/180
[58] Field of Search .............. 606/166, 161, 180; 128/757, 898; 30/169, 172, 303, 347; 408/211, 223, 227, 228; 144/218, 219, 228, 229

[56] References Cited

U.S. PATENT DOCUMENTS

| | | | |
|---|---|---|---|
| 2,249,906 | 5/1941 | Longoria | 128/305 |
| 2,480,737 | 3/1949 | Jayle | 128/305 |
| 3,074,407 | 1/1963 | Moon et al. | |
| 3,172,404 | 7/1965 | Copenhaver | 128/2.1 |
| 3,797,921 | 3/1974 | Kilmer et al. | |
| 3,976,077 | 8/1976 | Kerfoot, Jr. | 128/305 |
| 4,173,980 | 8/1979 | Curtin | 128/303 |
| 4,381,007 | 7/1983 | Doss | 128/303 |
| 4,423,728 | 1/1984 | Lieberman | 128/310 |
| 4,526,171 | 6/1985 | Schachar | 128/305 |
| 4,619,259 | 6/1986 | Graybill | 128/305 |
| 4,665,913 | 5/1987 | L'Esperance, Jr. | 128/303 |
| 4,665,914 | 5/1987 | Tanne | 128/305 |
| 4,688,570 | 8/1987 | Kramer et al. | 606/166 |
| 4,718,418 | 1/1988 | L'Esperance, Jr. | 128/303 |
| 4,724,522 | 1/1988 | Belgorod | 364/415 |
| 4,729,372 | 2/1988 | L'Esperance, Jr. | 128/303.1 |
| 4,750,491 | 6/1988 | Kaufman | 128/305 |
| 4,763,651 | 8/1988 | Kaufman | 128/310 |
| 4,770,172 | 10/1988 | L'Esperance, Jr. | 128/303 |
| 4,796,623 | 1/1989 | Krasner et al. | 128/305 |
| 4,798,204 | 1/1989 | L'Esperance, Jr. | 128/303 |
| 4,834,748 | 6/1989 | McDonald | 623/5 |
| 4,838,266 | 6/1989 | Koziol | 128/303.1 |
| 4,840,175 | 9/1989 | Peyman | 128/303.1 |
| 4,947,871 | 8/1990 | Grieshaber | 128/898 |

FOREIGN PATENT DOCUMENTS

| | | | |
|---|---|---|---|
| 0248569 | 12/1987 | European Pat. Off. | |
| 303174 | 2/1989 | European Pat. Off. | 606/166 |
| 2595243 | 9/1987 | France | 606/166 |
| 3433581 | 3/1986 | Germany | |
| 3707004 | 9/1988 | Germany | |

OTHER PUBLICATIONS

Mueller, et al Expil Eye Res. (1967) 6, 42–47 pp. 42–50 Some Experiments on Corneal Grinding.

Straatsma, et al Arch Ophthal–vol. 88, Sep. 1972 pp. 325–329 Stereotaxic Intraocular Surgery.

*Primary Examiner*—Michael H. Thaler
*Attorney, Agent, or Firm*—Head & Johnson

[57] ABSTRACT

Refractive error of the cornea is corrected by a scraping procedure performed within a vacuum chamber formed above the cornea.

44 Claims, 5 Drawing Sheets

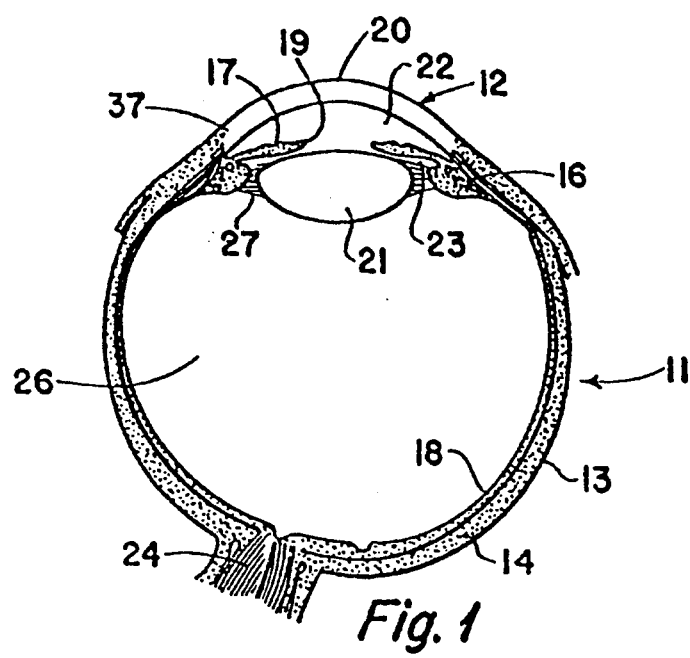
Fig. 1
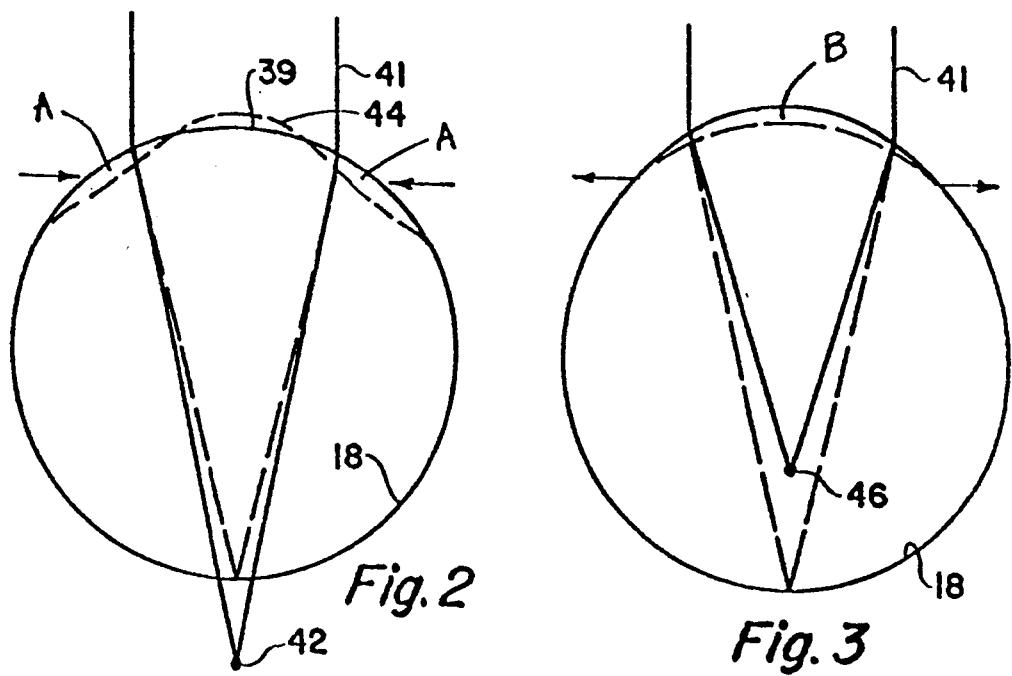
Fig. 2
Fig. 3

METHOD AND APPARATUS FOR SURGICALLY PROFILING THE CORNEA USING VACUUM

RELATED APPLICATIONS

This is a continuation of copending application Ser. No. 07/939,856 filed on Sep. 2, 1992, now abandoned, which is a continuation of Ser. No. 894,162 filed on Jun. 3, 1992, now abandoned, which is a continuation of Ser. No. 592,601 filed on Oct. 4, 1990, now abandoned, which is a continuation-in-part of Ser. No. 450,672 filed on Dec. 14, 1989, now U.S. Pat. No. 5,063,942.

BACKGROUND OF THE INVENTION

This invention relates to a method and apparatus for adjusting the shape of components of the eye and more particularly to making fixed changes in the corneal curvature to correct refractive error.

Deviations from the normal shape of the corneal surface produce errors of refraction in the visual process. The eye in a state of rest, without accommodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia is an error of refraction in which, with the eye at rest, parallel rays from distant objects are brought to focus behind the retina. Divergent rays from near objects are focused still further back. In one aspect of hyperopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accommodate, i.e., increase the convexity of its lens, or a convex lens of sufficient strength to focus rays on the retina must be placed before the eye.

Myopia is that refractive condition in which, with accommodation completely relaxed, parallel rays are brought to focus in front of the retina. One condition which commonly causes myopia is when the corneal curvature is steepened, thus the refraction of rays is greater as the rays pass through the refractive surfaces of the cornea, and the over-refracted rays converge or focus in front of the retina in the vitreous of the eye. When the rays reach the retina they become divergent, forming a circle of diffusion and consequently a blurred image. A concave lens is used to correct the focus of the eye for myopia.

The normal treatment of these classic forms of refractive error of the eye is with the use of eyeglasses or contact lenses, both of which have well-known disadvantages to the user. It has been estimated that 60 million pairs of eyeglasses and 3 million pairs of contact lens are sold annually.

Recent research has been directed to operative techniques to change the refractive condition of the eye. Such techniques are generally referred to as "keratorefractive techniques". Two such techniques are more particularly called keratophakia and keratomileusis. Keralomileusis involves the regrinding of a corneal lamella into a meniscus or hyperopic lens to correct myopia or hyperopia. A corneal optical lathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut as a contact lens would be, i.e., to the optical power required to effect the desired optical correction of the cornea. In keratomileusis, the anterior corneal lamella is shaped by the lathe and in keratophobia, it is the corneal stroma of a donor eye that is shaped by the lathe. These techniques have a broad application in the correction of high hyperopic and myopic errors. These procedures require radial cutting of the cornea about the periphery of the graft which weakens the cornea so that pressure from fluids below the incisions pushes up under the cuts and flattens the curvature of the cornea. This flattening of the cornea results in refractive errors to the eye not compensated for by the graft. Suturing in these operations also causes radial asymmetry of the cornea which consequently promotes astigmatic error in this regard. Sutures also cause scarring of the corneal tissue, which scar tissue loses its transparency. Surgical correction of astigmatism is accomplished by asymmetrically altering the corneal curvatures. The effect of a peripheral distorting force may be easily visualized by imagining an inflated balloon with a spherical surface being compressed between the palms of the hands. Because the volume of air in the balloon is constant, the surface area remains constant. The previously spherical anterior surface is distorted meridional as a result of compressing the diameter between the hands so that the curvature changes without changing the circumference of the surface. The meridian passing over the balloon between the extended fingers steepens, while the uncompressed meridian at right angles thereto flattens as its diameter lengthens in proportion to the shortening of the compressed diameter. This demonstrates the effect that may result from slight variations in the symmetrical patterns or intentional asymmetrical patterns attempted to be accomplished during surgical procedures and attendance suturing. It is thus seen that present procedures in keratorefractive techniques are best limited to situations where other more standard corrective practices are found ineffective. It is readily seen that the limiting factors in such surgical techniques is the gross complexity involved not only with multiple incisions in corneal tissue for affecting the procedures but also complex suturing patterns, resulting in gross restructuring of the eye. The eye is thus faced with a difficult job of adjusting to this trauma.

Over the past few years developments have been made in the use of lasers as a means to reshape the cornea in an attempt to get rid of refractive errors. In these processes, pulsed lasers remove tissue from the cornea by shaving off or vaporizing portions of the corneal surface to cause it to flatten. The most common type is an Exemer laser. The fundamental effect of such a laser on tissue is a photochemical one, the breaking of molecular bonds with so much energy that the tissue fragments fly from the surface at supersonic speeds, leaving behind a discreet space. The process has been designated as ablative photodecomposition or photoablation.

The use of Exemer lasers require delivery of the beam to the eye in a controlled manner requiring that the homogenous beam be appropriately managed and focused because the optical elements must withstand the high energy photons and because the beam must be shaped to a non-uniform configuration to create the new non-uniform optical surface of the cornea. Such delivery system contains multiple components including lenses to expand or focus the beam, mirrors to direct the beam, modulators to homogenize the beam, masks to shape the beam, and detectors to measure the intensity and configuration of the beam. Current models range from a simple collection of lenses and masks to complex robots with components that control not only the laser parameters but also the optical and mechanical components. Because the process is dealing with submicron (less than 0.00001 of a meter) accuracy, great demands are placed upon such systems for stability, even though the interaction of the laser and tissue lasts only microseconds.

Using the system requires exquisite technical and biological control to modulate corneal shaping.

Another laser treatment process focuses light, like a magnifying glass, to boil away tissue one cell at a time, instead of carving away the surface. One problem is adequate control to prevent the process from cutting through a layer of corneal tissue known as Bowman's membrane—a section of the eye that does not regenerate.

SUMMARY OF THE INVENTION

It is therefore an object of the present invention to provide a new and improved keratorefractive technique involving method and apparatus for changing the shape of the optical zone of the cornea to correct refractive errors of hyperopia (far-sightedness), myopia (near-sightedness), and astigmatism, whereby a non-spherical surface exists on the eye system and the simplicity of the technique virtually eliminates the chance of error or further complications resulting from gross disturbances of the eye system.

With this and other objects in view, the present invention contemplates a method and apparatus that can only be described as scraping, sculpting, or removing portions of the cornea for the purposes of correcting refractive error in human cornea. For the purposes of this invention and that of said co-pending application, Ser. No. 450,672, the action will be called "scraping".

Another object of the invention is to provide mechanical apparatus capable of easily being used by a surgeon for scraping the cornea in order to correct refractive errors of hyperopia, myopia, and astigmatism which includes means to provide consistency in depth and configuration of the surface.

Another object of this invention is to provide method and apparatus for scraping the cornea wherein the cornea is maintained in a more rigid posture during the procedure to eliminate flexure of the cornea and thus provide greater accuracy in determining predicable amounts of corneal material to be removed. This is accomplished by creating a vacuum in the operative space above the cornea during the process.

Specifically, the method objects of this invention involve the surgical reprofiling of the corneal portion of an eye of humans, to change the corneal radius and thus correct refractive errors. The steps include creating a placido ring keratograph of a simulated cornea having the correct refractive qualities. Next, an actual keratograph of the cornea is created. The two kerotographs are compared to determine the amount of refractive error, i.e. whether it would be hyperopia, myopia, or astigmatism.

A reprofiling tool is constructed to include a plurality of scraper blades of shape sufficient to change a corneal radius to that of the simulated cornea. The reprofiling tool is then positioned within a holding sleeve that is contiguously positioned upon said eye such that the scraper blades will contact the cornea. A vacuum is created in the chamber above the cornea wherein the scraping tool is positioned. The scraping tool is then rotated or oscillated with the axial movement of the scraping tool being changed and indexed until the corneal radius has been corrected to that of the simulated or ideal cornea.

The apparatus used to achieve the objects of this invention specifically includes a cylindrical positioning ring having a resilient vacuum ring means on its bottom side for temporary attachment to the sclera portion of an eye which surrounds the cornea that is to be reprofiled. A plurality of positioning pins exist on the top side of the positioning ring and a vacuum means is provided for communication with the vacuum ring. A cylindrical holding sleeve includes means at the bottom of the holding sleeve to interconnect with the positioning pins of the cylindrical positioning ring. A flexible and preferably clear tubing member extends from the bottom of the holding sleeve to seal against the cornea. Fine Screw threads of a given pitch, preferably about 40 threads per inch, are formed on the interior or exterior portion of the holding sleeve. Threadably connected thereto is a guide sleeve having screw threads of the same pitch as the threads of the holding sleeve for rotatable attachment with the holding sleeve. A scraping tool is adapted to be rotatably and axially received within the positioning ring, the holding sleeve, and the guide sleeve. A seal means is provided between the scraping tool, the guide sleeve and/or holding sleeve. A collar means existing on the scraping tool allows it to be rotatably supported upon the guide sleeve. A plurality of blades at the bottom of the scraper tool are designed to be of a shape sufficient to scrape away portions of the cornea to achieve the desired corrective curvature.

BRIEF DESCRIPTION OF THE DRAWINGS

FIG. 1 is a schematic illustration of a horizontal section of the eye.

FIG. 2 is a schematic illustration of a hyperopic eye showing adjustment of the cornea to shorten the radius of curvature.

FIG. 3 is a schematic illustration of a myopic eye system showing adjustment of the cornea to increase its radius and thus flatten the corneal slope.

DETAILED DESCRIPTION OF THE PREFERRED EMBODIMENT

Figure 4:
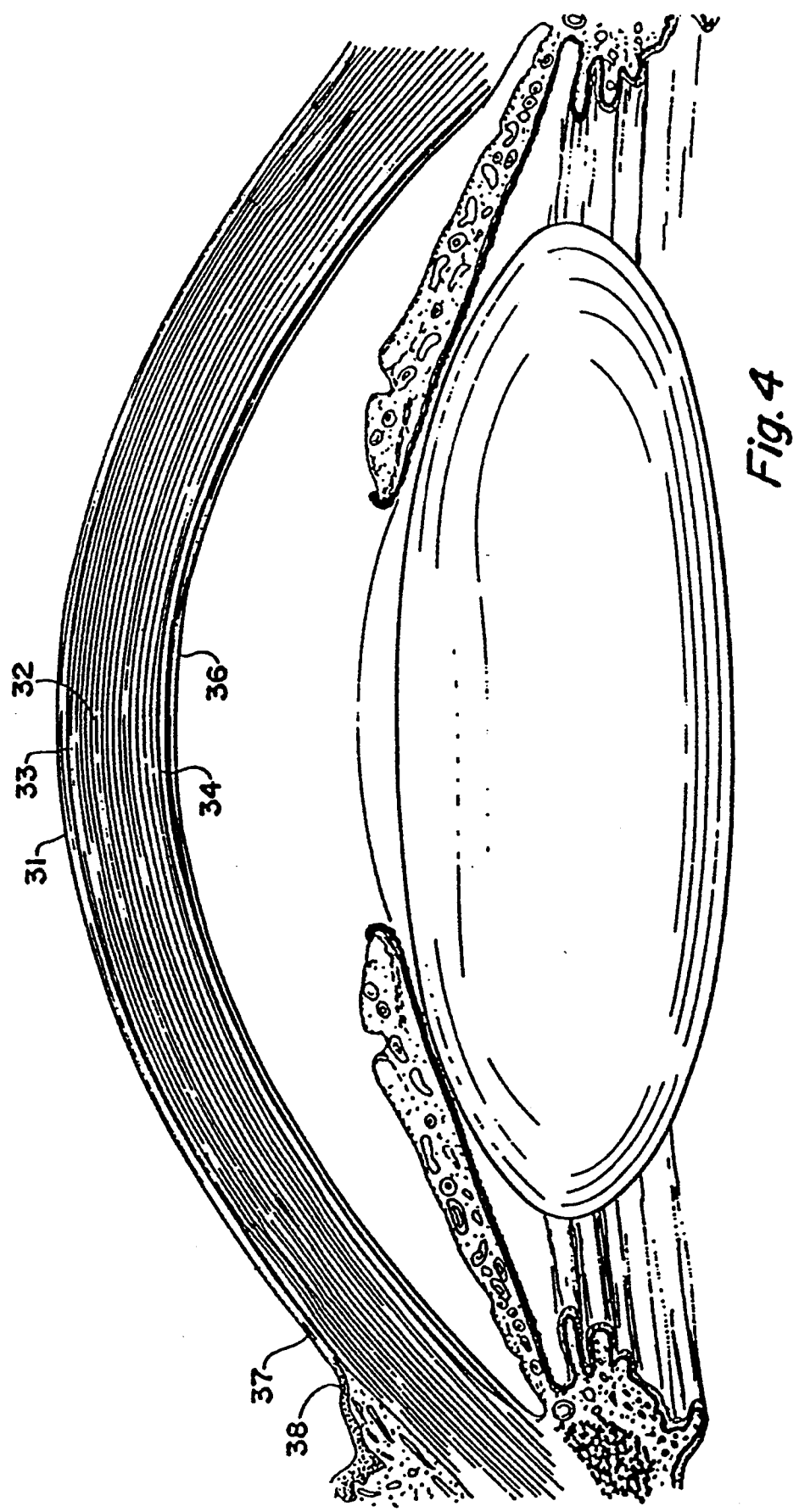
FIG. 4 is a detailed schematic illustration of a horizontal section of the frontal portion of an eye showing the various layers of the cornea.

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion, the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 15 and iris 17. The choroid generally functions to maintain the retina. The ciliary muscle is involved in suspending the lens and accommodation of the lens. The iris is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina. It contracts also to accommodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina is a part of the brain arising as an outgrowth from the fore-brain, with the optic nerve 24 serving as a fibre tract connecting the retina part of the brain with the fore-brain. A layer of rods and cones, lying just beneath a pigmented epithelium on the anterior wall of the retina, serve as visual cells or photoreceptors which transform physical energy (light) into nerve impulses.

The vitreous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and vitreous 26. Its axial diameter varies markedly with accommodation. A ciliary zonule 27, consisting of transparent fibers passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another, giving rise to astigmatism. A central third of the cornea is called the optical zone with a slight flattening taking place outwardly thereof as the cornea thickens towards it periphery. Most of the refraction of the eye takes place on the surface of the cornea.

Referring next to FIG. 2 of the drawings, the globe of an eye is shown having a cornea 12 with a normal curvature represented by the solid line 39. If parallel rays of light 41 pass through the corneal surface 39 of FIG. 2, they are refracted by the corneal surfaces to converge eventually near the retina 18 of the eye. The diagram of FIG. 2 discounts, for the purposes of this discussion, the refractive effect of the lens or other portions of the eye. The eye depicted in FIG. 2 is hyperopic and thus the rays of light 41 are refracted to converge at point 42 behind the retina. If a peripheral band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exaggeration) following the dotted line 44. The rays of light 41 are then refracted from the steeper surface 44 at a greater angle to direct the refracted rays into focus at shorter distance, such as directly on the retina 18.

FIG. 3 shows a similar eye system to that of FIG. 2 except that the so-called normal corneal curvature of FIG. 3 causes the light rays 41 to refract into focus at a point 46 in the vitreous which is short of the retinal surface 18. This is typical of a myopic eye. If chord 43 of the cornea is expanded uniformly outwardly as shown by the arrows, the walls of the cornea are flattened. Light rays 41 refracted by the now-flattened corneal surface will be refracted at a smaller angle and thus converge at a more distant point such as directly on the retina 18.

Referring now to FIG. 4, a more detailed drawing of the anterior portion of the globe shows the various layers of the cornea comprising an epithelium 31. Epithelial cells on the surface thereof function to maintain transparency of the cornea. These epithelial cells are rich in glycogen, enzymes and acetylcholine and their activity regulates the corneal corpuscles and controls the transport of water and electrolytes through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other and crossing the whole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descemet's membrane. It is a strong membrane sharply defined from the stroma and resistant to pathological processes of the cornea.

The endothelium 36 is the most posterior layer of the cornea and consists of a single layer of cells. The limbus 37 is the transition zone between the conjunctiva 38 and sclera 13 on the one hand and the cornea 12 on the other.

Figure 5:
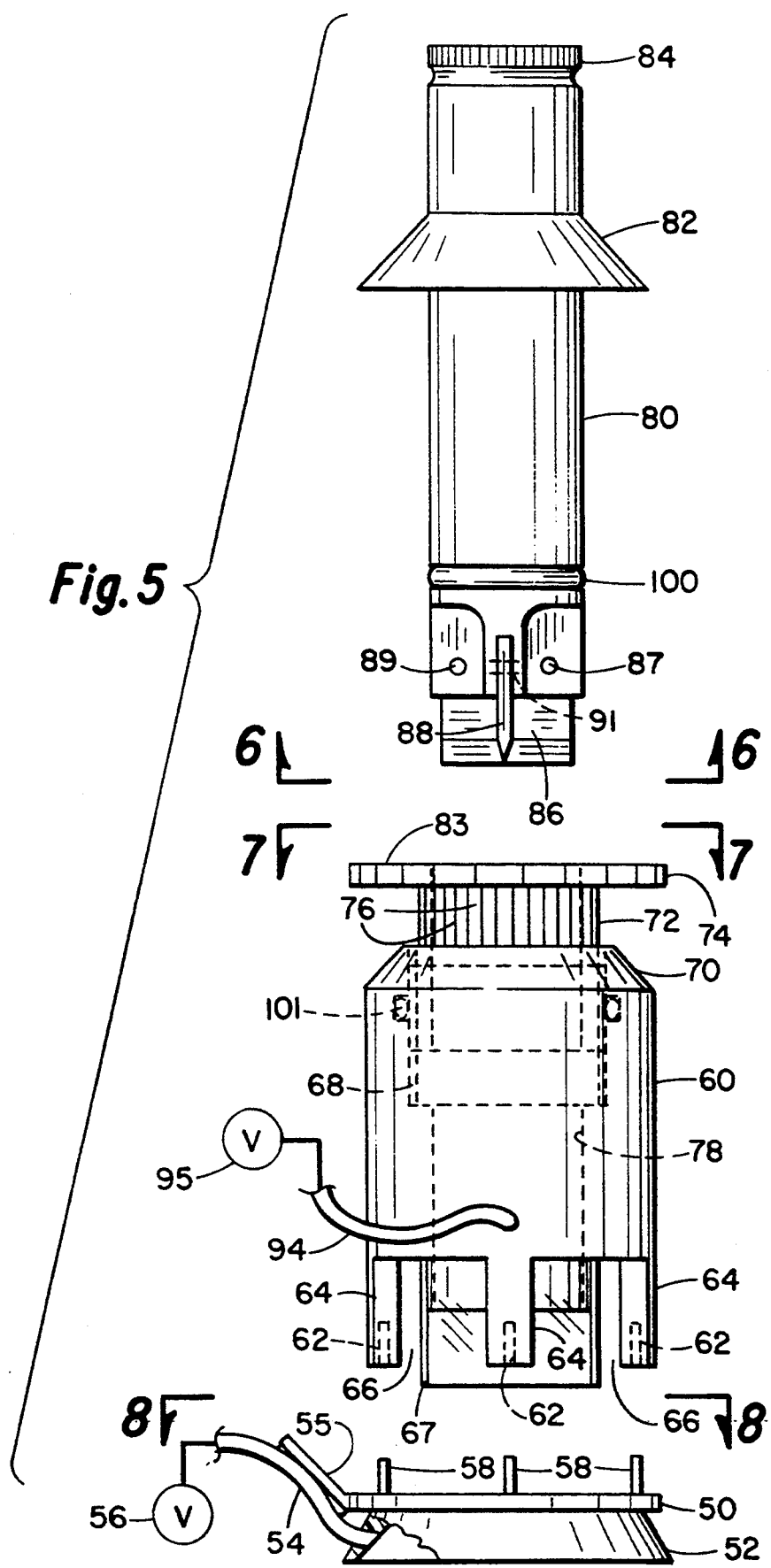
FIG. 5 is an exploded view showing the basic components of the apparatus of this invention.
Figure 6:
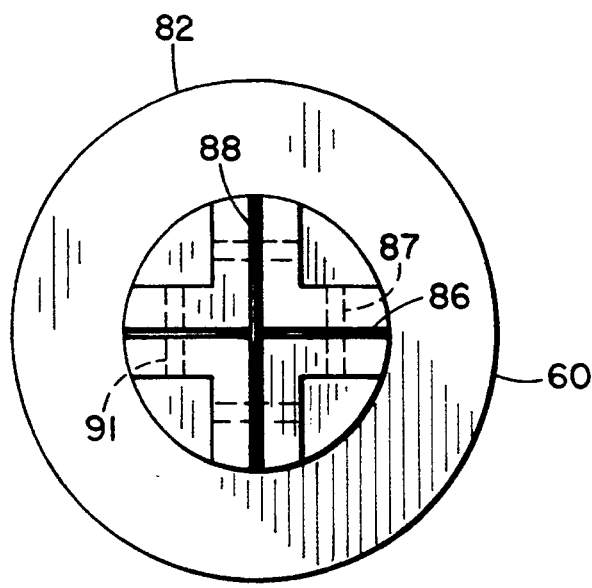
FIG. 6 is an end view of the reprofiling tool taken along the line 6—6 of FIG. 5.
Figure 7:
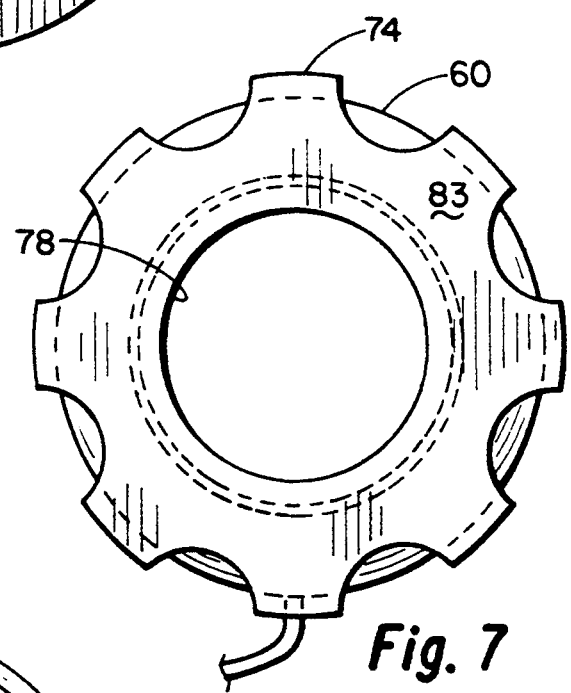
FIG. 7 is a top view of the tool holder taken along the line 7—7 of FIG. 5.
Figure 8:
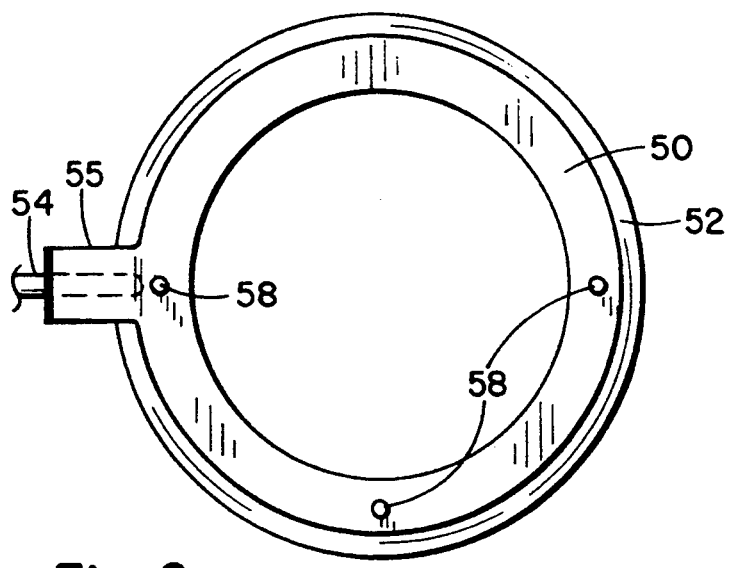
FIG. 8 is a top view of the positioning ring taken along the line 8—8 of FIG. 5.
Figure 9:
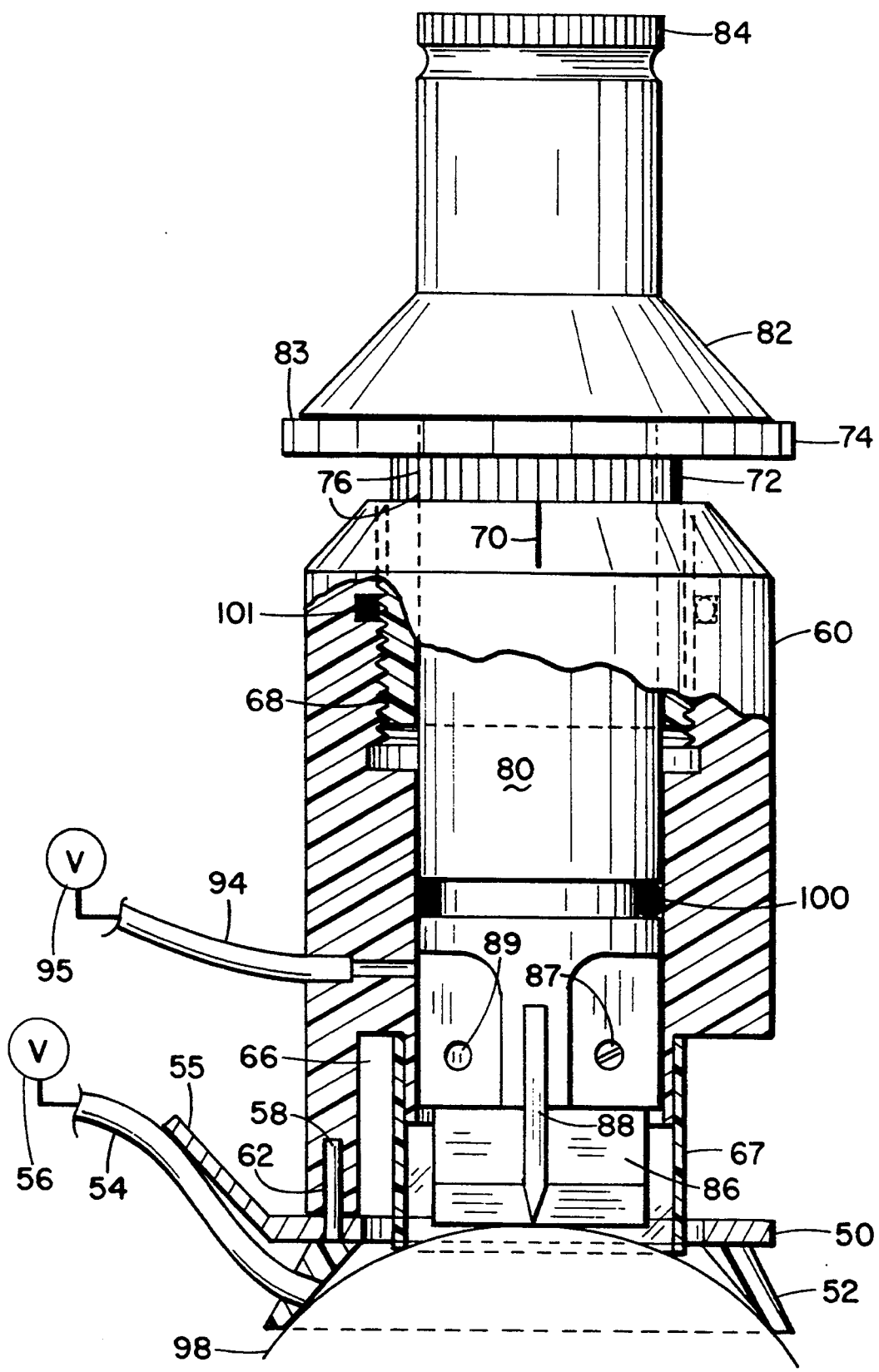
FIG. 9 is an assembly view, partly cut-away to show the apparatus of the invention.

Referring now to FIGS. 5–9, the assembly of the basic parts of the apparatus are shown in exploded and assembled views. These parts comprises a cylindrical positioning ring 50 having a resilient vacuum ring 52 extending from the bottom side of the positioning ring for contact with the eye of the patient being treated. A vacuum hose 54 provides communication from the inside of the resilient ring 52 and a vacuum pump source means 56 as a means to retain the assembled parts upon the eye for surgical procedures herein described. A plurality of positioning pins 58 are provided on the top side of the positioning ring to receive the cylindrical holding sleeve 60, the pins being adapted to be received through openings 62 in legs 64 of holding sleeve 60. Visual inspection openings 66 are provided between the legs for use by the surgeon or technician performing the process. A translucent, flexible, e.g. vinyl, cylinder 67 is centrally positioned at the bottom of the holding sleeve, which, when in use, will contact the outer portion of the cornea. The interior of the cylindrical holding sleeve 60 includes a plurality of screw threads 68 along a portion of its length, the threads being a very fine thread, e.g. of a pitch equal to 40 threads per inch. An indicia or marker 70 is provided in the body of the cylindrical holding sleeve so as to provide a visual measuring point for the surgeon relative to the rotatable position of a micrometer-like guide sleeve 72 which includes exterior threads to match threads 68 of the cylindrical holding sleeve. The guide sleeve includes an outer knob portion 74 and indicia generally designated by the numeral 76, e.g. millimeter markings on the lower portion of the guide sleeve which function to provide the amount of axial movement of the guide sleeve. The interior surface 78 of the cylindrical holding sleeve is adapted to rotatably receive a scraping tool 80. A conduit 94 communicates the interior of the holding sleeve with a vacuum source 95. The scraping tool includes a collar 82 which is adapted to rest upon the top surface 83 of the guide sleeve 72 for movement upwardly or downwardly therewith. The top end of the scraping tool can include a knurled grip portion 84 for rotation and/or oscillation by the surgeon. Positioned along the body of the scraping tool is O-ring 100 to seal against interior surface 78. An upper O-ring 101 frictionally engages the threads of a guide sleeve 72 to prevent inadvertent turning. This, along with the cylinder 67, forms a vacuum chamber above the cornea 98. At the bottom of the scraper tool are a plurality of blades 86 and 88 which are retained within the body of the scraping tool 80 by pins 87, 89, and 91. The blades 86 and 88 are retained transverse to the longitudinal axis of the scraping tool 80. The blades 86 and 88 as used in the invention are of surgical steel. The scraping tool 80 of FIG. 5 is adapted to provide a scraping operation upon the cornea over the top center thereof for myopia refractive error, i.e. near-sightedness, which will effectively lengthen the corneal radius of curvature as described relative to FIG. 3. To correct for hyperopia (far-sightedness), the scraping tool blades as shown and described in FIG. 8 of Ser. No. 450,672 are utilized. The blades are adapted to contact the outer anterior portion of the cornea in order to shorten the effective radius thereof, that is, the blades will be adapted to contact the area A as shown in FIG. 2 whereas the scraping tool 80 of FIG. 5 will be adapted to sculpt the area B of FIG. 3.

The operation of the apparatus and methods of surgery are accomplished by first taking optical measurements of the eye as to the shape of the cornea and to determine the refractive error, for example, the shape the cornea should have in order for that eye to operate in an optically correct manner—i.e. correct refractive errors. Typically, a kerotograph photographic image using a placido-ring target such as described in U.S. Pat. No. 3,797,921 is used. The photograph is of reflected light from the placido rings upon a standard spherical surface of the same size as the cornea in question, creating an image in the same manner as a topographic contour map. Subsequently, the topographic survey of the eye to be corrected is made for comparison purposes and to provide the surgeon with the necessary information for correcting the refractive errors. Once this occurs, the operation will proceed by placing the positioning ring 50 over the eye. The size of this ring may vary for different operations but is preferably of size wherein the resilient vacuum ring 52 will rest upon the sclera of the eye concentric about the cornea. Once the cylindrical positioning ring 50 is in place, the cylindrical holding sleeve 60 is then positioned thereupon by the engagement of openings 62 with positioning pins 58. Resilient vinyl seal tubing or cylinder 67 contacts the outer circumference of the cornea to seal therewith. Thereafter, the scraping tool 80 is inserted within the cylindrical holding sleeve 60 to a position where the bottom of the knife-edge blades 86 and 88 will initially contact the cornea. As shown in U.S. application Ser. No. 450,672, now U.S. Pat. No. 5.063,942 and incorporated herein by reference, the determination of contact of the tool blades with the cornea can be achieved electrically. See FIG. 11 of the aforesaid application. By rotating the guide sleeves 72 in incremental amounts as dictated by the caliper or measuring scales 70 and 76, the surgeon can continue to increase the depth of the scraping operation. Scraping of the cornea occurs by hand rotation of the scraping tool 80 although other mechanical or motor operated means are within the scope of this invention.

In myopic conditions, the scraping tool 80 of FIG. 5 is utilized. During the operation, the knife-edge blades press upon the corneal surface which becomes depressed and thus gives a larger contact surface with the blades resulting in a larger diameter of sculptured surface. The scraping action is accentuated in proportion to the pressure between the cornea and the blade. With a partial vacuum formed in the chamber above the cornea, the cornea becomes less yieldable and semi-rigid. The extent of rigidity is a function of the amount of vacuum. Pressures between five-eighths ($\frac{5}{8}$) to three-fourths ($\frac{3}{4}$) atmosphere or six (6) to ten (10) inches of Mercury (Hg) appear to be preferable, although not limiting to the purposes of this invention. It has been found that this allows the tool to have a greater positive 'feel' during the procedure with more predictable results in removal of corneal material to achieve the correct contour. The resulting effect is a lengthening of the refractive radius in that portion of the cornea under the blade. When the tool is removed, the cornea returns to its normal contour except that the radius over the top center thereof is now longer than it was initially. As a result, refractive light through the cornea now focuses upon the retina. The scraping action occurs by the surgeon in incremental movement by rotating the guide sleeve 72 relative to the cylindrical holding sleeve 60 utilizing the incremental measuring indicia 76 relative to pointer or other indicia 70. As one example, the guide sleeve is graduated into 25 micrometer divisions to provide 0.001" adjustments for each marked division of rotation. Through use, the surgeon or technician begins to decide the amount of downward movement needed to achieve the required changes in the cornea by the rotation and/or oscillation of the knives. The rotation for a period of a few seconds will result in removal of small amounts of corneal material from the cornea. The tool can be removed and/or kerotographic photographs taken to determine if the refractive error has been corrected. Since the apparatus and the surgical methods deal with very small increments of movement in the corneal reprofiling process, it is essential that the first contact setting be precise and accurate. Many times this can be done by visual means by the surgeon and in other instances electrical detecting means as previously described can be provided between the cornea and the tool blade to provide an exact setting of the tool which permits repeatable amounts of corneal removal.

What is claimed is:

1. A method of reprofiling a cornea comprising the steps of creating a vacuum chamber above a central portion of said cornea; positioning a corneal scraping tool having a sharpened knife edge substantially planar blade within said vacuum chamber such that said knife edge is perpendicular to a top center visual axis of said cornea; and turning said tool to scrape the anterior of said cornea to create a desired optically corrective curvature.

2. Apparatus for reprofiling the corneal portion of an eye of animals (including humans) to change the corneal radius and thus correct refractive errors, comprising
 a scraping tool, said tool having a plurality of sculpting blades of shape to scrape said cornea to said desired corneal radius;
 means to create a vacuum chamber above a central portion of said cornea;
 means to position said scraping tool within said vacuum chamber so as to be co-axial with a center axis of said cornea and means to rotate or oscillate said scraping tool relative to said cornea.

3. Apparatus of claim 2 including indexing means to provide indication of the axial location of said scraping tool relative to said cornea.

4. Apparatus of claim 2 wherein the amount of said vacuum is within the range of 6 to 10 inches of Hg.

5. A method of reprofiling a cornea comprising the steps of creating a vacuum chamber above a central portion of said cornea; positioning a corneal scraping tool with a substantially planar knife edge blade against a top center along a visual axis of said cornea within said vacuum chamber; and turning and axially advancing said tool around said visual axis to scrape the anterior of said cornea until a desired optically corrective curvature has been achieved.

6. A method of reprofiling the corneal portion of an eye to change the corneal radius and thus correct refractive errors, comprising the steps of:
 creating a keratograph of a simulated cornea having correct refractive qualities,
 creating an actual keratograph of said cornea,
 comparing said simulated keratograph with said actual keratograph to determine an amount of said refractive error,
 preparing a scraping tool to include at least one sharpened knife edge blade,
 positioning a holding sleeve over said cornea,
 creating a vacuum chamber within said holding sleeve above said cornea,
 positioning within said vacuum chamber said sharpened knife edge blade tangentially to and against a top center visual axis of said cornea,
 manually rotating or oscillating said blade coaxial with said visual axis,
 axially moving said scraping tool, and
 indexing the axial movement of said scraping tool until said corneal radius has been corrected to that of said simulated cornea.

7. The method of claim 6 wherein said axially moving of said scraping tool is done incrementally.

8. A method of correcting refractive error in an eye having a cornea defined anteriorly in the cornea by essentially an epithelium layer and a stroma portion comprising the steps of:
 creating a vacuum chamber above said cornea,
 positioning, within said vacuum chamber, a sharpened knife edge blade tangentially to and against a top center visual axis of said cornea,
 rotating or oscillating said knife edge about a vertical axis that is coincident with said visual axis of said cornea while simultaneously pressing and advancing said tool in controlled axial incremental amounts against said corneal epithelium layer and thence said stroma portion so as to scrape said cornea with said knife edge until said refractive error is substantially corrected.

9. The method of claim 8 wherein rotating or oscillating occurs manually.

10. A method of surgical reprofiling a cornea of an eye comprising the step of manually scraping, within a vacuum chamber formed above a central portion of said cornea, the top center anterior of said cornea by the rotation or oscillation of a sharpened substantially planar knife edge blade about a vertical axis that is coincident with a top center axis of said cornea to create a desired optically corrective curvature.

11. The method of claim 10 wherein said vertical axis is a visual axis of said eye.

12. Method of claim 10 including the step of axially advancing said blade incrementally against said cornea until said refractive error has been corrected.

13. A method of correcting refractive error in an eye having a cornea comprising the steps of:
 creating a vacuum chamber above said cornea,
 positioning, within said vacuum chamber, a sharpened knife edge blade tangentially to and against a top center visual axis of said cornea,
 rotating or oscillating said knife edge about a vertical axis that is coaxial with said visual axis of said cornea, so as to scrape said cornea with said knife edge until said refractive error has been substantially corrected.

14. The method of claim 13 wherein said rotating or oscillating occurs manually.

15. A method of correcting refractive error in an eye having a cornea comprising the steps of:
 creating a vacuum chamber above said cornea,
 positioning, within said vacuum chamber, a sharpened knife edge blade tangentially to and against a top center visual axis of said cornea,
 rotating or oscillating said knife edge about a vertical axis that is coincident with said visual axis of said cornea, so as to scrape said cornea with said knife edge until said refractive error has been substantially corrected.

16. A method of correcting refractive error in an eye having a cornea comprising the steps of:
 creating a vacuum chamber above said cornea;

within said vacuum chamber, pressing a sharpened knife edge blade tangentially to and against an anterior surface of said cornea;

rotating or oscillating said sharpened blade manually about a vertical axis that is substantially co-axial with a vertical visual axis of said cornea so as to scrape said cornea with said knife edge;

axially advancing said blade incrementally against said cornea until said refractive error has been corrected.

17. A method of reprofiling a cornea to a desired optically corrective curvature, comprising the steps of:
providing a vacuum chamber adjacent and above a central portion of said cornea;
positioning a sharpened knife-edge planar blade against said cornea within said vacuum chamber;
creating a vacuum within the vacuum chamber sufficient to make said cornea semi-rigid;
turning said knife-edge blade about a central axis of said cornea so as to scrape the anterior of said cornea to create a desired optically corrective curvature.

18. A method of reprofiling the corneal portion of an eye to change the corneal radius and thus correct refractive errors, comprising the steps of:
determining the amount of said refractive error;
creating a visual topographic keratograph of said corneal portion of said eye;
comparing said visual keratograph with a visual display means showing the corneal radius as corrected for said refractive error;
creating a vacuum chamber above a central portion of said cornea,
positioning, within said vacuum chamber, a sharpened knife edge planar blade scraping tool within a holding sleeve contiguous to and co-axial with a vertical visual axis at a top center of said cornea;
pressing said sharpened knife edge blade against said cornea;
manually rotating said tool about said vertical axis and continuing said rotating of said tool;
monitoring said keratograph until said refractive error has been substantially corrected.

19. Apparatus for reprofiling the corneal portion of an eye of animals (including humans) to change the corneal radius and thus correct refractive errors, comprising
a scraping tool, said tool having at least one planar knife edge blade of shape to scrape said cornea to said desired corneal radius;
means to create a vacuum chamber surrounding and above a central portion of said cornea;
means to position said scraping tool within said vacuum chamber and to rotate or oscillate said scraping tool relative to said cornea until a desired optically corrective curvature has been achieved.

20. Apparatus of claim 19 including indexing means to provide indication of the axial location of said scraping tool relative to said cornea.

21. Apparatus of claim 19 wherein the amount of said vacuum is within the range of 6 to 10 inches of Hg.

22. Apparatus of claim 19 wherein the amount of said vacuum is sufficient to make said cornea semi-rigid.

23. Apparatus of claim 22 wherein said holding sleeve and said guide sleeve include micrometer indexing means for incrementally measuring said axial movement of said scraping tool.

24. Apparatus for reprofiling the corneal portion of an eye of animals (including humans) to change the corneal radius and thus correct refractive errors, comprising
a cylindrical positioning ring having resilient vacuum ring means on its bottom side for temporary attachment to a sclera portion of said eye and surrounding said cornea to be reprofiled, positioning pins at a top side of said positioning ring, and vacuum means communicating with said vacuum ring means:
a cylindrical holding sleeve, means at a bottom of said holding sleeve to interconnect with said positioning pins, screw threads of a given pitch formed on an interior portion of said holding sleeve, and further having a resilient cylindrical sleeve at the bottom thereof in contact with said eye around said cornea;
a guide sleeve having screw threads of said given pitch formed exteriorly thereof for axial movement by rotatable attachment with said screw threads of said sleeve;
means to create a vacuum chamber within said holding sleeve above said cornea;
a scraping tool, said scraping tool adapted to be rotatably and axially received within said holding sleeve and said guide sleeve, a collar means on said scraping tool to rotatably support said scraping tool upon said guide sleeve, at least one knife edge blade at the bottom of said scraping tool;
means, within said vacuum chamber, to position said knife edge blade tangentially to and against a top center visual axis of said cornea; and
means to rotate or oscillate said knife edge blade coaxial with said visual axis of said eye so as to scrape said cornea until said refractive error has been substantially corrected.

25. Apparatus of claim 24 wherein said knife blade is concave.

26. Apparatus of claim 24 wherein said knife edge blade is such to effectively decrease the corneal radius.

27. Apparatus of claim 24 wherein said knife edge blade is such to effectively increase the corneal radius.

28. Apparatus of claim 24 wherein said knife edge blade comprises a plurality of radial blades, the bottom sharpened knife edges of which are transverse to the axis of said scraping tool.

29. Apparatus of claim 24 wherein said holding sleeve and said cylindrical sleeve are substantially transparent.

30. Apparatus of claim 29 wherein said pitch of said screw threads is 40 threads per inch.

31. Apparatus of claim 24 wherein said pitch of said screw threads is between 35 to 50 threads per inch.

32. Apparatus of claim 24 including means to axially advance said blade incrementally against said cornea until said refractive error has been corrected.

33. Apparatus of claim 32 including indexing means to provide indication of the axial location of said profiling tool relative to said cornea.

34. Apparatus for reprofiling the corneal portion of an eye of animals (including humans) to correct refractive errors, comprising
a positioning ring having means to be temporarily attached to and surround the eye relative to the cornea to be reprofiled;
a holding sleeve having means at its bottom to be retained by the position ring, a guide sleeve rotatable to the holding sleeve;

means to create a vacuum chamber within said holding sleeve centrally above said cornea;

a rotatable scraping tool adapted to be received within the holding sleeve and supported by the guide sleeve, a bottom end of the scraping tool being positionable within said vacuum chamber and comprised of sharpened knife edge substantially planar blade means, at said bottom end, to scrape a portion of the top center of said cornea necessary to correct said refractive errors.

35. Apparatus for reprofiling the corneal portion of an eye of animals (including humans) to correct refractive errors, comprising a positioning ring having means to be temporarily attached to and surround the eye relative to the cornea to be reprofiled;

a holding sleeve having means at its bottom to be retained by the position ring, a guide sleeve rotatable to the holding sleeve;

means to create a vacuum chamber within said holding sleeve centrally above said cornea;

a manually rotatable scraping tool adapted to be received within the holding sleeve and supported by the guide sleeve, a bottom end of the scraping tool being positionable within said vacuum chamber and comprised of sharpened knife edge substantially planar blade means, at said bottom end, to scrape a portion of the top center of said cornea necessary to correct said refractive errors.

36. Apparatus for reprofiling the corneal portion of an eye of animals (including humans) to change the corneal radius and thus correct refractive errors, comprising a cylindrical positioning ring having resilient vacuum ring means on its bottom side for temporary attachment to a sclera portion of said eye and surrounding said cornea to be reprofiled, positioning pins at a top side of said positioning ring, and vacuum means communicating with said vacuum ring means:

a cylindrical holding sleeve, means at a bottom of said holding sleeve to interconnect with said positioning pins, screw threads of a given pitch formed on an interior portion of said holding sleeve, and further having a resilient cylindrical sleeve at the bottom thereof in contact with said eye around said cornea;

a guide sleeve having screw threads of said given pitch formed exteriorly thereof for axial movement by rotatable attachment with said screw threads of said sleeve;

means to create a vacuum chamber within said holding sleeve centrally above said cornea;

a scraping tool, said scraping tool adapted to be rotatably and axially received within said holding sleeve and said guide sleeve, a collar means on said scraping tool to rotatably support said scraping tool upon said guide sleeve, at least one knife edge blade at the bottom of said scraping tool;

means, within said vacuum chamber, to position said knife edge blade; and means to rotate or oscillate said knife edge blade coaxial with said visual axis of said eye so as to scrape said cornea until said refractive error has been substantially corrected.

37. Apparatus for surgically reprofiling the corneal portion of an eye to a desired corneal radius and thus correct refractive errors, comprising:

a profiling tool, said tool having at least one sharpened substantially planar knife edge blade, means to create a vacuum chamber centrally above said cornea, means, within said vacuum chamber, to retain said knife edge relative to a top center of said cornea; and manual means to rotate or oscillate said blades against said top center of said cornea coaxially about a visual axis of said cornea.

38. Apparatus of claim 37 including indexing means to provide indication of the axial location of said profiling tool relative to said cornea.

39. Apparatus for correcting refractive error in an eye having a cornea with a visual axis, comprising:

a scraping tool, said tool having a sharpened knife edge blade at one end;

means to create a vacuum chamber above said cornea;

means, within said vacuum chamber, to position said knife edge blade tangentially to and against a top of said cornea at said visual axis; and means to rotate or oscillate said knife edge about said visual axis so as to scrape said cornea with said knife edge until said refractive error has been substantially corrected.

40. An implement for reprofiling the anterior surface of the cornea of an eye comprising:

a tool comprising a spindle having at one end thereof, constituting its inner end, a planar scraper blade means projecting endwise therefrom and extending outwardly from the spindle axis for scraping off portions of the anterior surface of the cornea by rotation or oscillation of the tool with the edge of said planar blade means in scraping engagement with said anterior surface of said cornea, means for holding the spindle for manual rotation coaxial with a visual axis of said cornea and for axial movement along said visual axis, means for mounting said holding means on the cornea of an eye in fixed relation to the eye with said planar scraper blade means at the inner end of the spindle in position for scraping engagement with said anterior surface of the cornea to scrape said surface in a circular manner, means to create a vacuum above a central portion of said cornea within a chamber formed by said means for mounting above the cornea, said planar scraper blade means being operative within said vacuum chamber, means for gauging the axial extension of the inner end of the spindle from the holding means to gauge the penetration of the edge of the blade means into the cornea for said scraping, and said gauging means being adjustable to vary the extension of the inner end of the spindle from the holding means.

41. An implement for surgically reprofiling the anterior surface of the cornea of an eye comprising:

a tool comprising a spindle having at one end thereof, constituting its inner end, a sharpened knife-edge planar scraper blade means projecting endwise therefrom and extending outwardly from the spindle axis for scraping off portions of the anterior surface of the cornea by rotation or oscillation of the tool with the sharpened edge of the planar blade means in scraping engagement with said anterior surface;

means for holding the spindle for rotation on its axis and for axial movement with the spindle extending at its said inner end out of said holding means;

means for mounting said holding means concentrically with a visual axis of said cornea in fixed relation to the eye with the planar blade means at the inner end of the spindle in position for scraping engagement with the anterior surface of the cornea to scrape said surface in a circular pattern about said visual axis;

means to create a vacuum in a space above a central portion of said cornea; and means for gauging the extension of the inner end of the spindle from the holding means to gauge the penetration of the edge of the planar blade means into the cornea for said scraping, said gauging means being adjustable to vary the extension of the inner end of the spindle from the holding means.

42. An implement for surgically reprofiling the anterior surface of the cornea of an eye comprising:

an axial tool having at one end thereof, constituting its inner end, a sharpened knife edge planar blade means projecting endwise therefrom and extending outwardly from the axis of the tool for correcting refractive error on the anterior surface of the corneal by manual rotation or oscillation of said tool with the sharpened edge of the blade means in engagement with said anterior surface, means for holding said tool for rotation about its axis and for controllable axial movement, means for mounting said holding means in fixed relation to said eye with said sharpened knife edge blade means at the inner end of the tool in position for engagement with said anterior surface of the cornea, means to create a vacuum within a chamber formed by said means for mounting above a central portion of the cornea, said knife edge blade means being operative within said vacuum chamber, means for gauging and adjusting the axial extension of the inner end of the tool from the holding means to gauge the locus of the edge of the blade means relative to said anterior surface of said cornea.

43. An implement for surgically reprofiling the anterior surface of the cornea of an eye comprising:

an axial tool having at one end thereof, constituting its inner end, a sharpened knife edge planar blade means projecting endwise therefrom and extending outwardly from the axis of the tool for correcting refractive error on the anterior surface of the corneal by rotation or oscillation of said tool with the edge of the blade means in engagement with said anterior surface, means for holding said tool for rotation about its axis and for controllable axial movement, means for mounting said holding means in fixed relation to said eye with said sharpened knife edge at the inner end of the tool in position for engagement with said anterior surface of the cornea, means to create a vacuum within a chamber formed by said means for mounting above a central portion of said cornea, said knife edge blade means being operative within said vacuum chamber, means for gauging and adjusting the axial extension of the inner end of the tool from the holding means to gauge the locus of the edge of said knife edge relative to said anterior surface of said cornea.

44. A method of reprofiling a cornea comprising the steps of creating a vacuum chamber above a central portion of said cornea; positioning a corneal scraping tool having a sharpened substantially straight knife edge blade within said vacuum chamber such that said knife edge is perpendicular to a top center visual axis of said cornea; and turning said tool to scrape the anterior of said cornea to create a desired optically corrective curvature.

* * * * *